US010726998B2

(12) United States Patent
Bushong et al.

(10) Patent No.: US 10,726,998 B2
(45) Date of Patent: Jul. 28, 2020

(54) FEEDTHROUGH DEVICE

(71) Applicant: Energizer Brands, LLC, St. Louis, MO (US)

(72) Inventors: William C. Bushong, Madison, WI (US); Gregory J. Davidson, Oregon, WI (US); Terrance W. Gurrie, Jr., Madison, WI (US); Sarah L. Westcott, Verona, WI (US)

(73) Assignee: Energizer Brands, LLC, St. Louis, MO (US)

( * ) Notice: Subject to any disclaimer, the term of this patent is extended or adjusted under 35 U.S.C. 154(b) by 0 days.

(21) Appl. No.: 16/068,318

(22) PCT Filed: Jan. 6, 2017

(86) PCT No.: PCT/IB2017/050059
§ 371 (c)(1),
(2) Date: Jul. 5, 2018

(87) PCT Pub. No.: WO2017/118946
PCT Pub. Date: Jul. 13, 2017

(65) Prior Publication Data
US 2019/0027313 A1 Jan. 24, 2019

Related U.S. Application Data

(60) Provisional application No. 62/276,649, filed on Jan. 8, 2016.

(51) Int. Cl.
*H01G 4/35* (2006.01)
*H01G 4/232* (2006.01)
(Continued)

(52) U.S. Cl.
CPC ............... *H01G 4/35* (2013.01); *H01G 4/232* (2013.01); *H01G 4/236* (2013.01); *H01M 2/06* (2013.01);
(Continued)

(58) Field of Classification Search
CPC .. H01G 4/35; H01M 2/06; H02G 3/22; A61N 1/3754
(Continued)

(56) References Cited

U.S. PATENT DOCUMENTS

| 4,129,690 A | 12/1978 | Jones et al. |
| 4,233,372 A * | 11/1980 | Bro .......................... H01M 2/08 |
| | | 429/174 |

(Continued)

OTHER PUBLICATIONS

Final Rejection Office Action on U.S. Appl. No. 14/192,558 dated Oct. 11, 2016 (5 pages).
(Continued)

*Primary Examiner* — Timothy J Thompson
*Assistant Examiner* — Michael F McAllister
(74) *Attorney, Agent, or Firm* — Alston & Bird LLP (57) ABSTRACT

A feedthrough device includes a body having longitudinally spaced first and second end faces and an inner surface defining an opening extending longitudinally through the body, a conductor extending within the opening of the body, and an insulator extending within the opening of the body transversely intermediate the conductor and the inner surface of the body to insulate the conductor from the body, where the conductor includes an interior portion surrounded by the insulator and an exterior portion extending beyond the insulator, the exterior portion having a diameter that is greater than a diameter of the interior portion.

20 Claims, 8 Drawing Sheets

(51) Int. Cl.
  *H01G 4/236* (2006.01)
  *H01M 2/06* (2006.01)
  *H02G 3/22* (2006.01)
  *H01G 9/008* (2006.01)
  *H01G 9/10* (2006.01)
  *A61N 1/375* (2006.01)

(52) U.S. Cl.
  CPC ............. *H02G 3/22* (2013.01); *A61N 1/3754* (2013.01); *H01G 9/008* (2013.01); *H01G 9/10* (2013.01)

(58) Field of Classification Search
  USPC ........................................................ 174/652
  See application file for complete search history.

(56) References Cited

U.S. PATENT DOCUMENTS

| | | | | |
|---|---|---|---|---|
| 5,643,694 | A * | 7/1997 | Heller, Jr. | H01M 2/06 174/152 GM |
| 6,670,074 | B2 | 12/2003 | Spillman | |
| 7,341,802 | B1 * | 3/2008 | Ota | H01M 2/0404 174/50.61 |
| 7,416,811 | B2 * | 8/2008 | Nakahara | H01M 2/22 429/161 |
| 8,932,750 | B2 * | 1/2015 | Cooley | H01G 11/78 429/179 |
| 9,209,438 | B2 | 12/2015 | Pollack et al. | |
| 9,281,507 | B2 * | 3/2016 | Bruch | H01M 2/1094 |
| 2003/0096162 | A1 * | 5/2003 | Lasater | C03C 27/042 429/184 |
| 2003/0134194 | A1 * | 7/2003 | Lasater | C03C 8/24 429/181 |
| 2004/0191621 | A1 * | 9/2004 | Heller, Jr. | H01M 2/065 429/181 |
| 2005/0255380 | A1 * | 11/2005 | Lasater | C03C 27/042 429/184 |
| 2008/0038634 | A1 * | 2/2008 | Bushong | H01M 4/24 429/206 |
| 2008/0210455 | A1 | 9/2008 | Pollack et al. | |
| 2012/0152611 | A1 * | 6/2012 | Fisher | B64D 37/32 174/653 |
| 2014/0272544 | A1 * | 9/2014 | Bruch | H01M 2/1094 429/163 |
| 2014/0315075 | A1 | 10/2014 | Bilek et al. | |
| 2017/0149028 | A1 * | 5/2017 | Kroll | B23K 26/206 |

OTHER PUBLICATIONS

International Search Report and Written Opinion received in PCT/IB2017/050059 dated Apr. 21, 2017 (12 pages).
International search report issued for PCT/IB2017/050059, dated Apr. 21, 2017.
Non-Final Office Action on U.S. Appl. No. 14/192,558 dated Feb. 27, 2017 (10 pages).
Non-Final Rejection Office Action on U.S. Appl. No. 14/192,558 dated Jul. 7, 2016 (9 pages).
Notice of Allowance on U.S. Appl. No. 14/192,558 dated Jul. 7, 2017 (8 pages).

* cited by examiner

FEEDTHROUGH DEVICE

CROSS-REFERENCE TO RELATED PATENT APPLICATIONS

This application is a U.S. 371c National Stage Application of International Application No. PCT/IB2017/050059, filed Jan. 6, 2017, which claims priority from U.S. Application No. 62/276,649, filed Jan. 8, 2016, both of which are incorporated herein by reference in their entireties. This application is related to U.S. application Ser. No. 14/192,558, filed Feb. 27, 2014, which claims priority from U.S. Application No. 61/777,777, filed Mar. 12, 2013, both of which are incorporated herein by reference in their entireties.

BACKGROUND

The present invention relates generally to a feedthrough device and, more particularly, to a hermetic electrical feedthrough device.

A feedthrough device is an electrical device that is used to transmit electricity through a wall, typically the wall of a sealed housing. For example, in some instances, a feedthrough device may be utilized to transmit electricity through a wall of an electro-chemical housing (e.g., a terminal extending into a battery), a wall of a heated housing (e.g., a thermocouple extending into a furnace), a wall of pressurized housing (e.g., a communication link extending into a submersible vessel), or the like. As such, in some applications, a feedthrough device may experience a harsh environment on at least one side of the wall through which it extends (e.g., the feedthrough device may be exposed to corrosive matter, increased pressure, and/or increased temperature on the inside of the sealed housing). Feedthrough devices may also be used as thermal feedthrough devices, which are used to transmit thermal energy through a wall via a conductor suitable for heat transfer.

There is a need, therefore, for a feedthrough device that enables the transfer of electricity through a wall of a housing and effectively withstands the harsh environment within the housing to prevent the transfer of other matter into, and out of, the housing, while minimizing manufacturing time and cost.

SUMMARY

One embodiment of the invention relates to a feedthrough device including a body having longitudinally spaced first and second end faces and an inner surface defining an opening extending longitudinally through the body, a conductor extending within the opening of the body, and an insulator extending within the opening of the body transversely intermediate the conductor and the inner surface of the body to insulate the conductor from the body, where the conductor includes an interior portion surrounded by the insulator and an exterior portion extending beyond the insulator, the exterior portion having a diameter that is greater than a diameter of the interior portion.

Another embodiment of the invention relates to a feedthrough device including a body having longitudinally spaced first and second end faces and an inner surface defining an opening extending longitudinally through the body, a conductor extending within the opening of the body, and an insulator extending within the opening of the body transversely intermediate the interior portion of the conductor and the inner surface of the body to insulate the conductor from the body, where the conductor includes an interior portion surrounded by the insulator and an exterior portion extending beyond the insulator and where the exterior portion includes a flattened portion.

In some embodiments, a distance between the first end face and the second end face of the body is at least three times the diameter of the interior portion of the conductor.

In some embodiments, an outer diameter of the body is more than four times the diameter of the interior portion of the conductor.

In some embodiments, the feedthrough device is one of multiple of feedthrough devices with each feedthrough device insulated from the other feedthrough devices.

In some embodiments, a compressive yield strength of the conductor is greater than a compressive yield strength of the insulator and wherein a compressive yield strength of the body is greater than the compressive yield strength of the insulator.

In some embodiments, the insulator is compressed at least 5%. In some embodiments, the insulator is compressed at least 10%. In some embodiments, the insulator is compressed at least 15%. In some embodiments, the insulator is compressed at least 25%. In some embodiments, the insulator is compressed at least 50%. In some embodiments, the insulator is compressed less than 85%. In some embodiments, the insulator is compressed less than 80%. In some embodiments, the conductor is compressed more than 1%. In some embodiments, the conductor is compressed more than 5%. In some embodiments, the conductor is compressed more than 10%. In some embodiments, the conductor is compressed more than 15%. In some embodiments, the conductor is compressed more than 20%. In some embodiments, the conductor is compressed more than 25%.

In some embodiments, the body has at least one indentation formed longitudinally into at least one of the first and second end faces, a portion of the inner surface of the body being displaced transversely against the insulator in correspondence with the at least one longitudinal indentation to crimp the insulator and conductor within the opening of the body and maintain a hermetic seal across the feedthrough device. In some embodiments, the longitudinal depth of the at least one indentation is at least 20% of the distance between the first end face and the second end of the body. In some embodiments, longitudinal depth of the at least one indentation is at least 25% of the distance between the first end face and the second end of the body. In some embodiments, the longitudinal depth of the at least one indentation is at least 30% of the distance between the first end face and the second end of the body. In some embodiments, the longitudinal depth of the at least one indentation is less than 40% of the distance between the first end face and the second end of the body. In some embodiments, the longitudinal depth of the at least one indentation is less than 35% of the distance between the first end face and the second end of the body. In some embodiments, the longitudinal depth of the at least one indentation is less than 30% of the distance between the first end face and the second end of the body.

In some embodiments, the exterior portion includes a surface suitable for a welded connection.

In some embodiments, the body and the conductor are fabricated from the same metallic material and the insulator is fabricated from a polymeric material.

In some embodiments, the conductor is an electrical conductor.

In some embodiments, the conductor is a thermal conductor.

BRIEF DESCRIPTION OF THE DRAWINGS

Corresponding reference characters indicate corresponding parts throughout the several views of the drawings.

DETAILED DESCRIPTION

Figure 1:
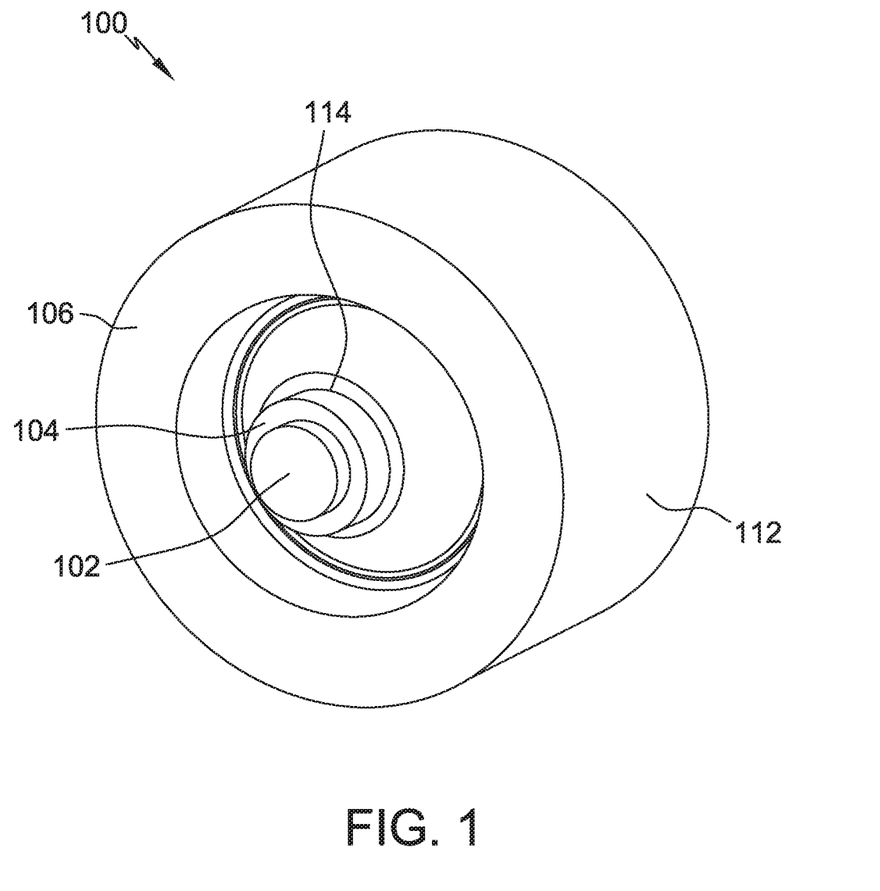
FIG. 1 is a perspective view of one embodiment of a feedthrough device.
Figure 2:
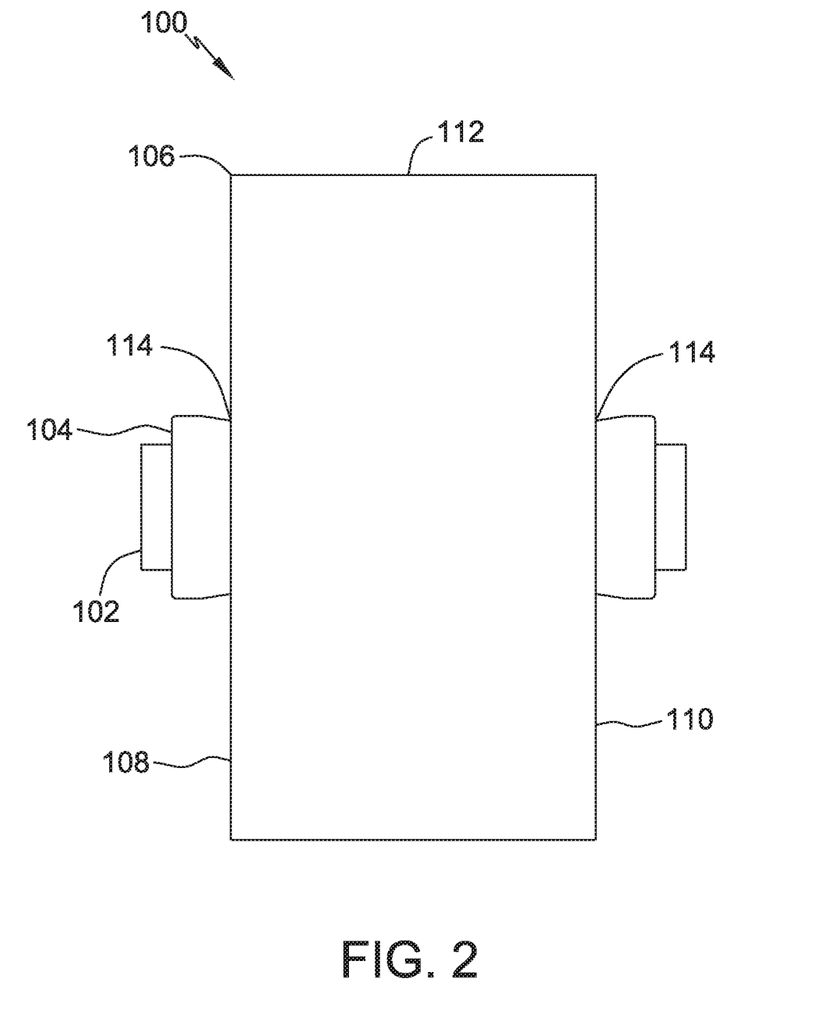
FIG. 2 is a side elevation of the feedthrough device of FIG. 1.
Figure 3:
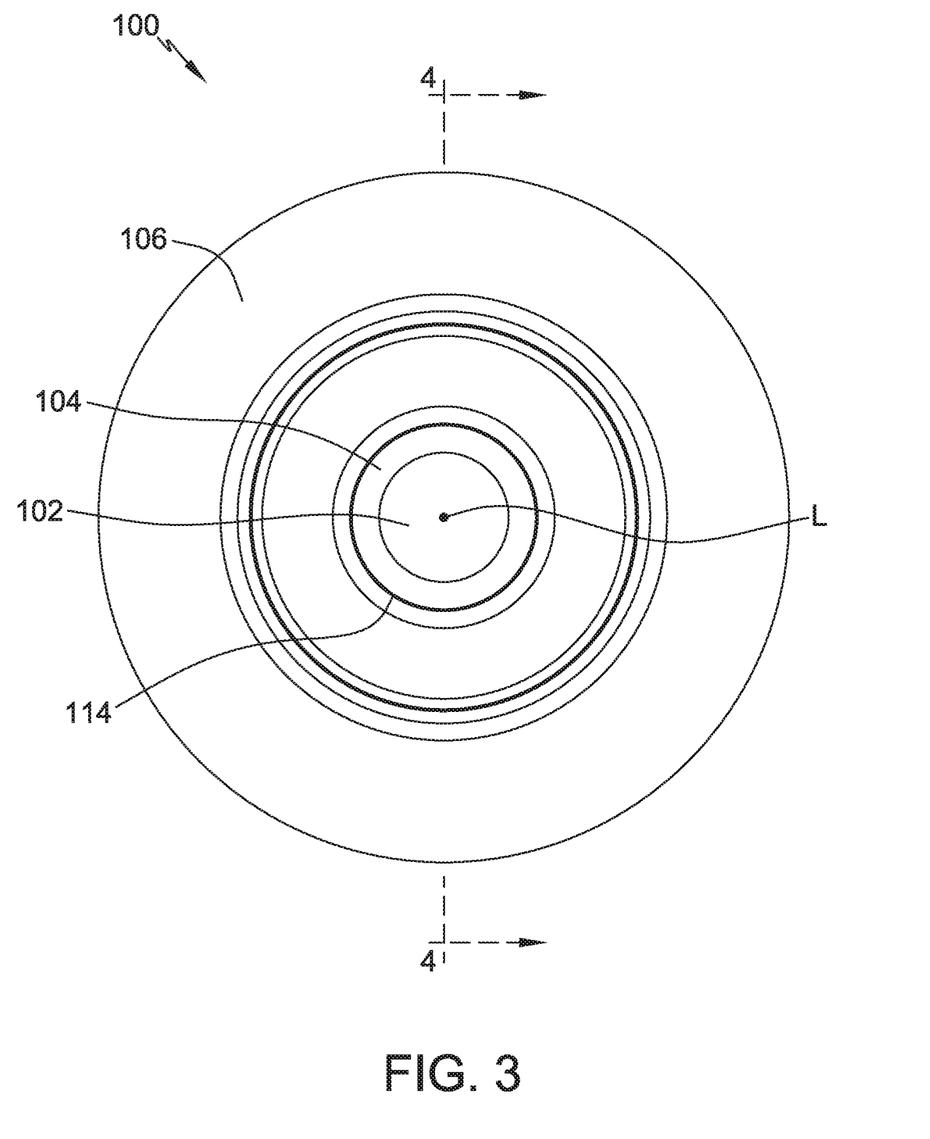
FIG. 3 is a top plan view of the feedthrough device of FIG. 1.

Referring now to the drawings, and in particular to FIGS. 1-3, a feedthrough device according to one embodiment is generally indicated by the reference numeral 100. The feedthrough device 100 includes a conductor 102, an insulator 104 enclosing at least a portion of the conductor 102, and a body 106 enclosing at least a portion of the insulator 104. In some embodiments, the conductor 102 is an electrical conductor. In some embodiments, the conductor 102 is a thermal conductor.

In the illustrated embodiment, the body 106 is all or part of a wall of a sealed housing such as, for example, the end wall of a lithium battery cell housing. The body 106 has longitudinal end faces, referred to herein as a first face 108 (e.g., an exterior face of the battery cell housing), and a second face 110 (e.g., an interior face of the battery housing) longitudinally spaced from the first face 108. A third (e.g., transversely outer) face 112 extends longitudinally between the first face 108 and the second face 110 and broadly defines an outer surface of the body. The body 106 also has a longitudinally extending opening 114 therethrough defining an inner surface of the body as well as a longitudinal axis L of the body (FIG. 4).

The conductor 102, the insulator 104, and the inner surface of the body defined by the opening 114 have a cross-sectional profile that is substantially circular (FIG. 3). However, in other embodiments the conductor 102 (as well as the insulator 104 and the inner surface of the body 106) may have any cross-sectional shape such as, for example, a square, a rectangle, a pentagon, a hexagon, an octagon, or other suitable shape. While the opening 114 is substantially centrally located on the body 106 in the illustrated embodiment, the opening 114 may be located elsewhere on the body 106 without departing from the scope of this invention.

As used herein, the term "inner," "inward," or any variation thereof is a directional modifier referring to a disposition that is relatively closer to the longitudinal axis L, and the term "outer," "outward," or any variation thereof is a directional modifier referring to a disposition that is relatively farther from the referenced location or component. Additionally, as used herein, the term "length" or any variation thereof refers to a dimension defined by the longitudinal axis L, and the term "width" or any variation thereof refers to a dimension extending perpendicular to the longitudinal axis L. The term "transverse" refers to a direction generally normal to the longitudinal axis L.

Figure 4:
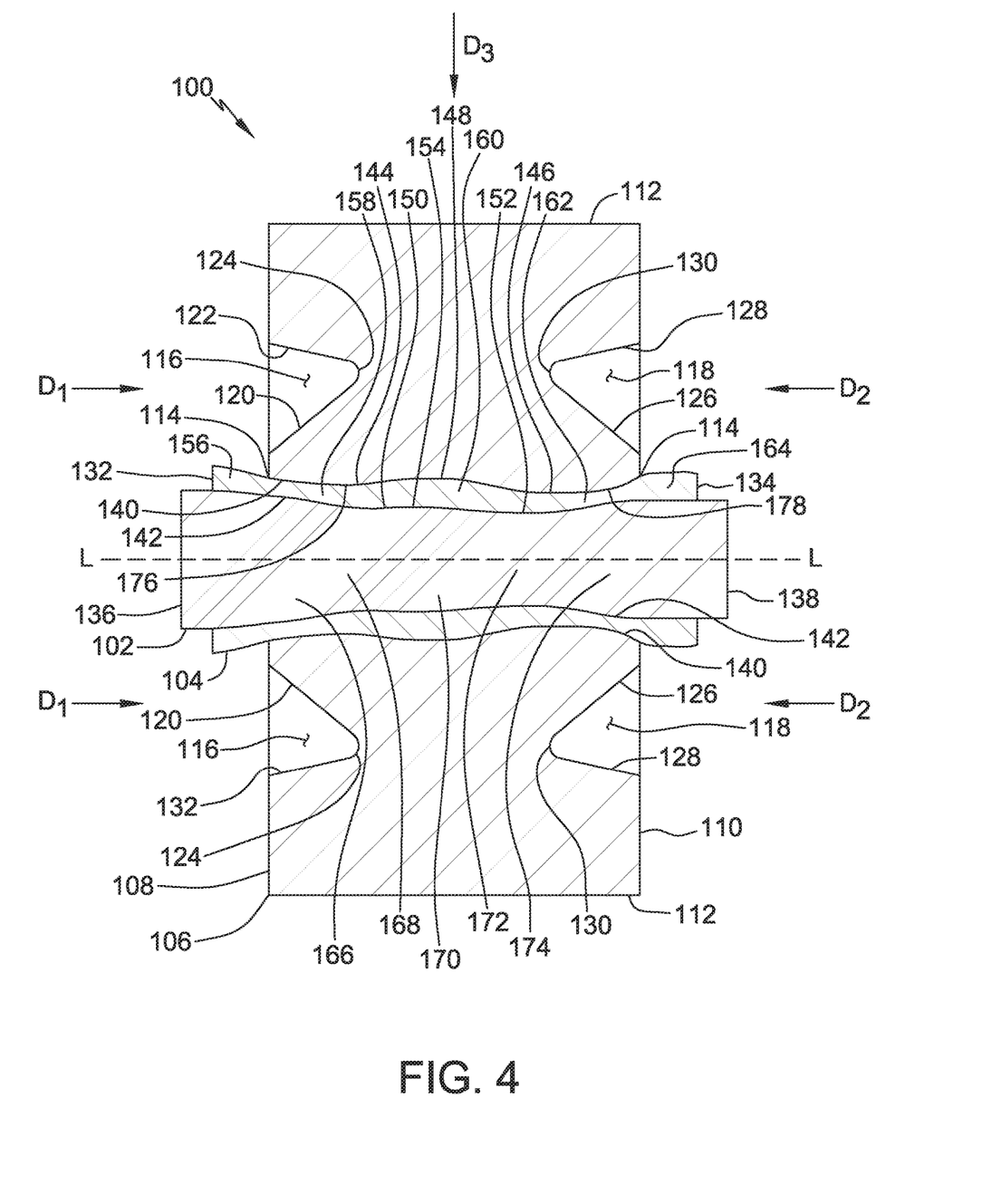
FIG. 4 is a cross-section of the feedthrough device of FIG. 3 taken along plane 4-4.

With reference now to FIG. 4, the conductor 102 and the insulator 104 are received in and extend through the opening 114 of the body 106. A first indentation 116 is formed into the first face 108, and a second indentation 118 is formed in the second face 110, with each of the indentations 116, 118 being annular about the opening 114 (and hence the longitudinal axis L). In other embodiments, the body 106 may have another suitable size and shape (e.g., the body 106 may have a polygonal shape such as, for example, a square or rectangle).

Similarly, the indentations 116, 118 may not be annular in other embodiments (e.g., at least one of the annular indentations 116, 118 may instead be a plurality of arc-shaped indentation segments forming a broken, seemingly scored annulus, or at least one of the indentations 116, 118 may have a plurality of linear or non-linear segments that are arranged about the opening 114). Alternatively, the body 106 may have any suitable configuration that enables the feedthrough device 100 to function as described herein. It should also be noted that, as used herein, the phrase "extending circumferentially about" or any variation thereof refers to extending about the perimeter of an object having any suitable shape (e.g., a square, a rectangle, a triangle, etc.) and is not limited to extending about the perimeter of an object having a circular shape.

The illustrated first indentation 116 extends generally longitudinally into the first face 108 of the body 106 and more particularly has a generally V-shaped contour that is defined at least in part by a first inner segment 120 and a first outer segment 122 that are joined together at a first vertex 124. The first inner segment 120 has a generally linear contour and is oriented obliquely relative to the longitudinal axis L.

Similarly, the illustrated second indentation 118 extends generally longitudinally into the second face and has a generally V-shaped contour that is defined at least in part by a second inner segment 126 and a second outer segment 128 that are joined together at a second vertex 130. The second inner surface 126 also has a generally linear contour and is oriented obliquely relative to the longitudinal axis L. Notably, in the illustrated embodiment, the oblique orientation of the first inner segment 120 and the second inner segment 126 relative to the longitudinal axis L facilitates displacement of material of the body 106, and more particularly the inner surface of the body at the opening 114, transversely inward toward the longitudinal axis L.

More particularly, a V-shaped crimping tool is pressed into each of the first and second faces 108, 110 to form the indentations 116, 118 as described in more detail below. Also, each of the first indentation 116 and the second indentation 118 is sized to have a length (e.g., from its respective face 108, 110 longitudinally to its respective vertex 124, 130) of about one-fourth of a length of the body 106 as measured from the first face 108 to the second face 110 at the opening (e.g., the length of the inner surface of the body). In other embodiments, the indentations 116, 118 may have any suitable contour and/or length that facilitates enabling the body 106 to function as described herein.

The illustrated conductor 102 and insulator 104 extend through the opening 114 of the body 106 with the insulator 104 enclosing (e.g., extending circumferentially about) at least a portion of the conductor 102 such that the insulator 104 is disposed between the conductor 102 and the body 106 to insulate the body from the conductor. The insulator 104 has a first end 132 and a second end 134, with the first and second ends 132, 134 of the insulator extending longitudinally outward of the body 106 at the opposite ends of the opening 114. The illustrated conductor 102 also has opposite first and second ends 136, 138 that extend longitudinally outward of the body 106 at the opening 114, and more particularly longitudinally outward beyond the ends 132, 134 of the insulator 104. In some embodiments, the illustrated body 106 has a length (from the first face 108 to the second face 110) that is at least about two-times to three-times a width of the conductor 102 as measured before any crimping operation that deforms the conductor 102.

As such, the insulator 104 contacts the body 106 along an annular outer contact zone 140 extending longitudinally from the first face 108 to the second face 110 of the body 106 (e.g., along the inner surface defined by the opening 114). The insulator 104 contacts the conductor 102 along an annular inner contact zone 142 extending from the first end 132 of the insulator 104 to the second end 134 thereof. In the illustrated embodiment, the outer contact zone 140 between the insulator 104 and inner surface of the body 106 has an undulating contour along its length that includes: a first outer valley segment 144 adjacent the first face 108 of the body 106; a second outer valley segment 146 adjacent the second face 110 of the body 106; and an outer peak segment 148 disposed axially between the first outer valley segment 144 and the second outer valley segment 146.

Similarly, the illustrated inner contact zone 142 has an undulating contour along its length that includes: a first inner valley segment 150 adjacent the first face 108 of the body 106; a second inner valley segment 152 adjacent the second face 110 of the body 106; and an inner peak segment 154 disposed axially between the first inner valley segment 150 and the second inner valley segment 152. In other embodiments, the outer contact zone 140 and/or the inner contact zone 142 may have any suitable contours (e.g., any suitable arrangement of peaks and valleys) that facilitate enabling the insulator 104 to function as described herein.

In addition to the insulator 104 having contact zones 140, 142 that undulate, a width of the insulator 104, as measured from the inner contact zone 142 to the outer contact zone 140, varies along its length from the first end 132 to the second end 134 of the insulator 104. More specifically, in longitudinally sequential order from the first end 132 to the second end 134 of the insulator 104, the width of the insulator 104 varies as follows: a first wider region 156; a first narrower region 158; an intermediate wider region 160; a second narrower region 162; and a second wider region 164. The first narrower region 158 and the second narrower region 162 are narrower than the first wider region 156, the intermediate wider region 160, and the second wider region 164.

In the illustrated embodiment, the first wider region 156 of the insulator 104 extends from the first end 132 of the insulator 104 to the first face 108 of the body 106, and the second wider region 164 of the insulator 104 extends from the second end 134 of the insulator 104 to the second face 110 of the body 106 (i.e., the insulator 104 is wider outside of the channel 114 of the body 106 than at the first and second faces 108, 110 of the body 106). Additionally, the intermediate wider region 160 of the insulator 104 is confined, in its axial extension, to an area between the vertices 124, 130 of the indentations 116, 118 and, therefore, extends through the outer and inner peak segments 148, 154 of the outer and inner contact zones 140, 142, respectively.

As such, the first narrower region 158 corresponds generally with the first inner segment 120 of the first indentation 116 and, therefore, extends through the first inner valley segment 150 and the first outer valley segment 144. Similarly, the second narrower region 162 corresponds generally with the second inner segment 126 of the second indentation 118 and, therefore, extends through the second inner valley segment 152 and the second outer valley segment 146. In other embodiments, the width of the insulator 104 may have any suitable number of narrower regions and wider regions arranged in any suitable manner along its length and having any suitable widths relative to one another that facilitates enabling the insulator 104 to function as described herein. Additionally, in order to facilitate optimal deformation (e.g., compression) of material in the conductor 102, the insulator 104 and the body 106 during the crimping operation described below, the illustrated insulator 104 has a width (from the inner contact zone 142 to the outer contact zone 140) of about one third to one half of the width of the conductor 102 before the crimping operation is performed.

Similar to the insulator 104, the width of the conductor 102 also varies axially from the first end 132 to the second end 134 of the insulator 104. More specifically, in longitudinally sequential order from the first end 132 to the second end 134 of the insulator 104, the width of the conductor 102 varies as follows: a first wider region 166 longitudinally aligned with the first wider region 156 of the insulator 104; a first narrower region 168 longitudinally aligned with the first narrower region 158 of the insulator 104; an intermediate wider region 170 longitudinally aligned with the intermediate wider region 160 of the insulator 104; a second narrower region 172 longitudinally aligned with the second narrower region 162 of the insulator 104; and a second wider region 174 longitudinally aligned with the second wider region 164 of the insulator 104. Alternatively, the width of the conductor 102 may have any suitable number of narrower regions and wider regions along the length of the insulator 104 and be arranged in any suitable manner that facilitates enabling the conductor 102 to function as described herein.

In the illustrated embodiment, the conductor 102 and/or the body 106 are fabricated from an electrically conductive material such as, for example, any one (or combination of) the following metallic materials: metals alloys; steel alloys; aluminum alloys; stainless steel; nickel; titanium; gold; silver; platinum; niobium; molybdenum; aluminum; tin; copper; brass; bronze; zinc; and invar or another nickel alloy (such as the "Monel" material or the "Inconel" material available from Special Metals Corporation). For purposes described in more detail below, the material composition of the illustrated conductor 102 and the illustrated body 106 are sufficiently ductile so as to permit material deformation upon crimping, while also having a sufficiently low elastic modulus so as to inhibit material spring-back after the deformation that results from the crimping. In other embodiments, the conductor 102 and the body 106 may be fabricated from any suitable materials that facilitate enabling the conductor 102 and the body 106 to function as described herein.

The illustrated insulator 104 is fabricated from an electrically non-conductive polymeric material composition that exhibits superior mechanical, thermal, and chemical properties, such as, for example, any one (or combination of) the following polymeric materials: polyvinylidene fluoride (PVDF); polytetrafluoroethylene (PTFE); polysulfone (PSU); polyether ether ketone (PEEK); chlorotrifluoroethylene (CTFE); fluorinated ethylene propylene (FEP); perfluoroalkoxy (PFA); a blend of polyphenylene oxide (PPO) and polystyrene (PS) (such as the "Noryl" material available from Sabic); polyetherimide (PEI); polyphenylene sulfide (PPS); and a polyimide (PI) film (such as the "Kapton" material or the "Cirlex" material available from DuPont). Alternatively, the insulator 104 may be fabricated from any suitable material that facilitates enabling the insulator 104 to function as described herein.

To assemble the feedthrough device 100, the conductor 102 and the insulator 104 are inserted through the opening 114 of the body 106 such that the insulator 104 separates (i.e., insulates) the body from the conductor along the entire inner surface of the body at the opening. Upon initial insertion of the conductor 102 and insulator 104 through the opening 114, the respective widths of the conductor 102 and insulator are uniform at least along the length of the inner surface of the body 106. In other words, if the feedthrough device 100 was to be viewed from the cross-sectional viewpoint of FIG. 4 prior to the crimping operation described below, the inner and outer contact zones 140, 142 would be substantially linear and thus parallel to the inner surface of the body and hence the longitudinal axis L (i.e., the contact zones 140, 142 would not undulate in the manner illustrated in FIG. 4).

After insertion of the conductor 102 and the insulator 104 through the opening 114, a first crimping tool (not shown) having an annular, generally V-shaped contour (mirroring the contour of the first indentation 116) is pressed into the first face 108 in a first direction D1 (i.e., longitudinally) that is substantially parallel to the longitudinal axis L. Because the material composition of the body 106 is sufficiently ductile, the configuration of the first crimping tool forms the first indentation 116 into the first face and results in displacing material of the body 106 at the inner surface of the body transversely inward toward the longitudinal axis L. This causes a first transverse annular bulge 176 in the inner surface of the body 106. The first transverse annular bulge 176 deforms (e.g., compresses and/or displaces) material of the insulator 104 and the conductor 102, thereby crimping the feedthrough device 100 near the first face 108 of the body 106.

More particularly, this crimping action forms the first outer valley segment 144 of the outer contact zone 140 and the first inner valley segment 150 of the inner contact zone 142 such that the first narrower region 158 longitudinally correspond with the first inner segment 120 of the first indentation 116. In other embodiments, the contour of the first crimping tool that is pressed into the first face 108 of the body 106 may not be annular but, rather, may be configured to suit other desirable patterns of the first indentation 116, as set forth above. Additionally, the first crimping tool may be pressed into the first face 108 in any suitable direction that facilitates displacing material of the body 106 as described herein (e.g., a direction that is other than substantially parallel to the longitudinal axis L).

Either before, after, or simultaneous to crimping the feedthrough device 100 by forming the first indentation 116, a second crimping tool (not shown) having an annular, generally V-shaped contour (mirroring the contour of the second indentation 118) is also pressed into the second face 110 in a second direction D2 (e.g., longitudinally) that is substantially parallel to the longitudinal axis L. Again, because the material composition of the body 106 is sufficiently ductile, the second crimping tool forms the second indentation 118 in the second face 110 and results in displacing material of the body 106 at the inner surface of the body transversely inward toward the longitudinal axis L. This causes a second transverse annular bulge 178 in the inner surface of the body 106. Forming this second annular bulge 178 deforms (e.g., compresses and/or displaces) material of the insulator 104 and the conductor 102, thereby crimping the feedthrough device 100 near the second face 110 of the body 106.

This crimping action forms the second outer valley segment 146 of the outer contact zone 140 and the second inner valley segment 152 of the inner contact zone 142 such that the second narrower region 162 is longitudinally aligned with the second inner surface 126 of the second indentation 118. In other embodiments, the contour of the second crimping tool that is pressed into the second face 110 of the body 106 may not be annular but, rather, may be configured to suit other desirable patterns of the second indentation 118, as set forth above. Additionally, the second crimping tool may be pressed into the second face 110 in any suitable direction that facilitates displacing material of the body 106 as described herein (i.e., a direction that is other than substantially parallel to the longitudinal axis L).

Notably, the first crimping tool and the second crimping tool may be one and the same (i.e., a single crimping tool may be used to indent both the first face 108 and the second face 110). Also, it is contemplated that in some alternative embodiments one of the first face 108 and the second face 110 may not be indented (i.e., the insulator 104 and the conductor 102 may be crimped by indenting only one of the first face 108 and the second face 110, thereby forming only one of the annular bulges 176, 178 within the opening 114). Moreover, it should be noted that while the bulges 176, 178 are annular in the illustrated embodiment due to the indentations 116, 118 being annular, the bulges 176, 178 may not be annular in other embodiments but, rather, may have configurations that suit alternative, non-annular indentation configurations, as set forth above.

As a result of crimping operations including the one-sided and two-sided crimping operations described herein, the intermediate wider region 160 of the insulator 104 is disposed longitudinally between the first and second narrower regions 158, 162 of the insulator 104 such that at least a portion of the intermediate wider region 160 of the insulator 104 is confined by the first annular bulge 176 and the second annular bulge 178 of the body 106. Additionally, the intermediate wider region 170 of the conductor 102 is also disposed longitudinally between the first and second narrower regions 158, 162 of the insulator 104 such that at least a portion of the intermediate wider region 170 of the conductor 102 is confined by the first narrower region 158 and the second narrower region 162 of the insulator 104.

Moreover, because the first and second wider regions 156, 164 of the insulator 104 (which are disposed exterior of the opening 114) are too wide to fit into the opening 114 after crimping (i.e., due, at least in part, to material of the insulator 104 being displaced longitudinally from within the opening 114 to exterior of the body 106), the first wider region 156 of the insulator 104 is kept to the exterior of the body 106 by the first face 108, and the second wider region 164 of the insulator 104 is kept to the exterior of the opening 106 by the second face 110.

With this arrangement, movement of the conductor 102, the insulator 104 and the body 106 relative to one another parallel to the longitudinal axis L (e.g., during thermal cycling due to creep or thermal expansion) is inhibited, and a hermetic seal is maintained across the feedthrough device 100 through the opening 114 of the body 106. Yet, despite this, the insulator 104 (e.g., the first narrower region 158 of the insulator 104 and the second narrower region 162 of the insulator 104) is still able to expand and contract to suit differences in coefficients of thermal expansion that may exist between the material composition of the conductor 102 and the material composition of the body 106 (i.e., in some embodiments, the body 106 may be fabricated from a first metallic material, and the conductor 102 may be fabricated from a second metallic material that is different than the first metallic material). Optionally, the inner surface of the body 106 along the outer contact zone 140, and/or the surface of the conductor 102 along the inner contact zone 142, may be roughened (e.g., via sandblasting, sanding, knurling, or peening) to further assist in inhibiting relative movement of the body 106, the insulator 104 and the conductor 102 along the longitudinal axis L after crimping.

In this manner, the feedthrough device 100 enables electrical transmission through a body (e.g., a wall of a housing) while preventing the transfer of gas, liquid, or solid matter through the body. Due to the geometry of the indentations 116, 118 formed by the crimping tool, and the location of the resultant deformation (e.g., compression) of the insulator 104, the feedthrough device 100 is able to accommodate the use of electrically conductive materials with different thermal expansion coefficients while maintaining hermeticity upon thermal cycling. The feedthrough device 100 also offers improved chemical resistance due to the wider array of metallic material compositions that are available for the body 106 and the conductor 102, and due to the wider array of polymeric material compositions that are available for the insulator 104. The materials and processes described herein for fabricating the feedthrough device 100 are relatively inexpensive, thus resulting in a low-cost assembly.

An additional benefit associated with the feedthrough device 100 is that the body 106 may be integrally formed as one with an object through which electrical transmission is desired (e.g., the body 106 may itself be the wall of the housing such as a battery cell housing into which electricity is to be transmitted, as opposed to the body 106 being formed separately from, and coupled to, the wall of the housing). This is possible because, as opposed to having the indentations 116, 118 formed in the third face 112 (e.g., outer surface) of the body 106 (i.e., as opposed to the crimping tool(s) being pressed transversely into the body 106 in a direction D3 that is substantially perpendicular to the longitudinal axis L of the channel 114), the indentations 116, 118 are formed longitudinally into the first and second faces 108, 110 (i.e., the crimping tool(s) are pressed into the body 106 in directions D1, D2 that are substantially parallel to the longitudinal axis L of the channel 114), meaning that the crimping operation can occur after the conductor 102 and the insulator 104 have already been inserted through the wall of the housing into which electricity is desired to be transmitted. Hence, in the illustrated embodiment, the third face 112 of the body 106 is not indented transversely for the purpose of crimping the conductor 102 and the insulator 104 (i.e., the third face 112 is free from an indentation that results in crimping of the insulator 104 and the conductor 102). In this manner, the feedthrough device 100 described herein facilitates eliminating the need for a body that is separate from, and coupled to, the wall of the housing after crimping.

The feedthrough device 100 described herein also alleviates various limitations associated with glass-to-metal seals and hermetic epoxy seals in feedthrough devices. More specifically, glass-to-metal feedthrough devices require that the housing and the conductive element have closely matched thermal expansion coefficients to that of the glass in order to prevent damage to the seal upon thermal cycling. As a result, in feedthrough devices having glass-to-metal seals, only a narrower array of materials is available for use as the material composition of the body, of which aluminum and other metals having higher coefficients of thermal expansion are likely excluded. Similarly, when compared to the feedthrough device described herein, feedthrough devices having epoxy seals are also limited in chemical compatibility across a narrower temperature range.

In some embodiments, the distance between the end face of the first end 136 of the conductor 102 and the end face of the second end 138 of the conductor 102 is at least three times the diameter of the conductor 102. In some embodiments, the outer diameter of the body 106 is at least four times the diameter of the conductor 102. In some embodiments, the compressive yield strength of the materials used to form the conductor 102 and the body 106 are greater than the compressive yield strength of the material used to form the insulator 104.

The crimping or coining operation to secure the conductor 102, the insulator 104, and the body 106 to one another (e.g., the crimping operation described above with reference to the feedthrough device 100) may compress the conductor 102 and the insulator 104 to varying degrees. Compression of the conductor 102 is measured by comparing the minimum outer diameter of a valley segment 150 or 152 after crimping to the outer diameter of the original uncompressed conductor 102 before crimping. In different embodiments, the conductor 102 is compressed more than 1%, more than 5%, more than 10%, more than 15%, more than 20%, and more than 25%. Compression of the insulator 104 is measured by comparing the minimum outer diameter of a valley segment 144 or 146 after crimping to the outer diameter of the original uncompressed insulator 104 before crimping. In different embodiments, the insulator 104 is compressed at least 5%, at least 10%, at least 15%, at least 25%, at least 50%, less than 85%, and less than 80%.

The crimping or coining operation to secure the conductor 102, the insulator 104, and the body 106 to one another (e.g., the crimping operation described above with reference to the feedthrough device 100) may form indentations 116, 118 of varying depths. Depth is measured longitudinally from the end face 108, 110 to the vertice 124, 130 of the indentation 116, 118. In different embodiments, the depth of the indentations 116, 118 compared to the length of the body 106 as measured from the first face 108 to the second face 110 at the opening (e.g., the length of the inner surface of the body) is at least 20%, at least 25%, at least 30%, less than 40%, less than 35%, and less than 30%.

Figure 5:
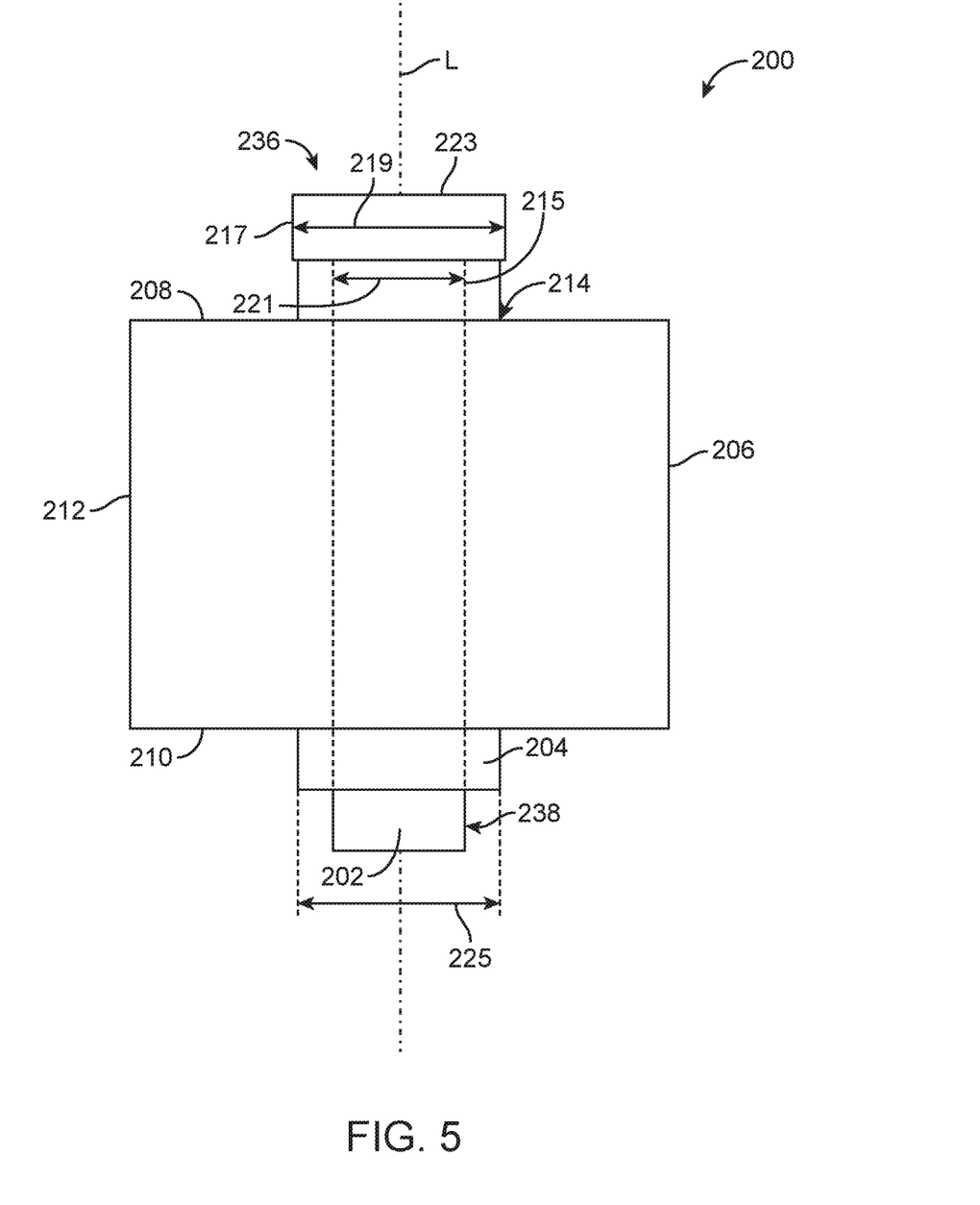
FIG. 5 is a side elevation view of one embodiment of a feedthrough device.

FIG. 5 illustrates a feedthrough device 200 according to an exemplary embodiment. The feedthrough device 200 is similar in many aspects to the feedthrough device 100. The feedthrough device 200 includes a conductor 202, an insulator 204 enclosing at least a portion of the conductor 202, and a body 206 enclosing at least a portion of the insulator 204.

In the illustrated embodiment, the body 206 is all or part of a wall of a sealed housing such as, for example, the end wall of a lithium battery cell housing. The body 206 has longitudinal end faces, referred to herein as a first face 208 (e.g., an exterior face of the battery cell housing), and a second face 210 (e.g., an interior face of the battery housing) longitudinally spaced from the first face 208. A third (e.g., transversely outer) face 212 extends longitudinally between the first face 208 and the second face 210 and broadly defines an outer surface of the body. The body 206 also has a longitudinally extending opening 214 therethrough defining an inner surface of the body as well as a longitudinal axis L of the body.

The conductor 202 has an interior portion 215 surrounded by the insulator 204 and an exterior portion 217 extending beyond the insulator 204 and located outside of the body 206. The diameter (or width) 219 of the exterior portion 217 is greater than the diameter (or width) 221 of the interior portion 215. As illustrated, the diameter 219 of the exterior portion 217 is substantially the same as the outer diameter (or width) 225 of the insulator 204. In some embodiments, the diameter 219 of the exterior portion 217 is greater than or less than the outer diameter 225 of the insulator 204.

The increased diameter 219 of the exterior portion 217 provides a relative large surface area on the end face 223 of the conductor 202. This relatively large surface area is particularly suitable for a welded connection and makes it easier to weld or otherwise attach additional components to the conductor 202 as compared to the feedthrough device 100. Easier welding can reduce assembly time, costs, and complexity. As illustrated, the end face 223 of the exterior portion 217 of the conductor is flat. The flat end face 223 is perpendicular to the longitudinal axis of the interior portion 215 of the conductor 202. In some embodiments, the feedthrough device 200 that includes two exterior portions 217, one formed at the first end 236 of the conductor 202 and the other formed at the second end 238 of the conductor 202.

Figure 6:
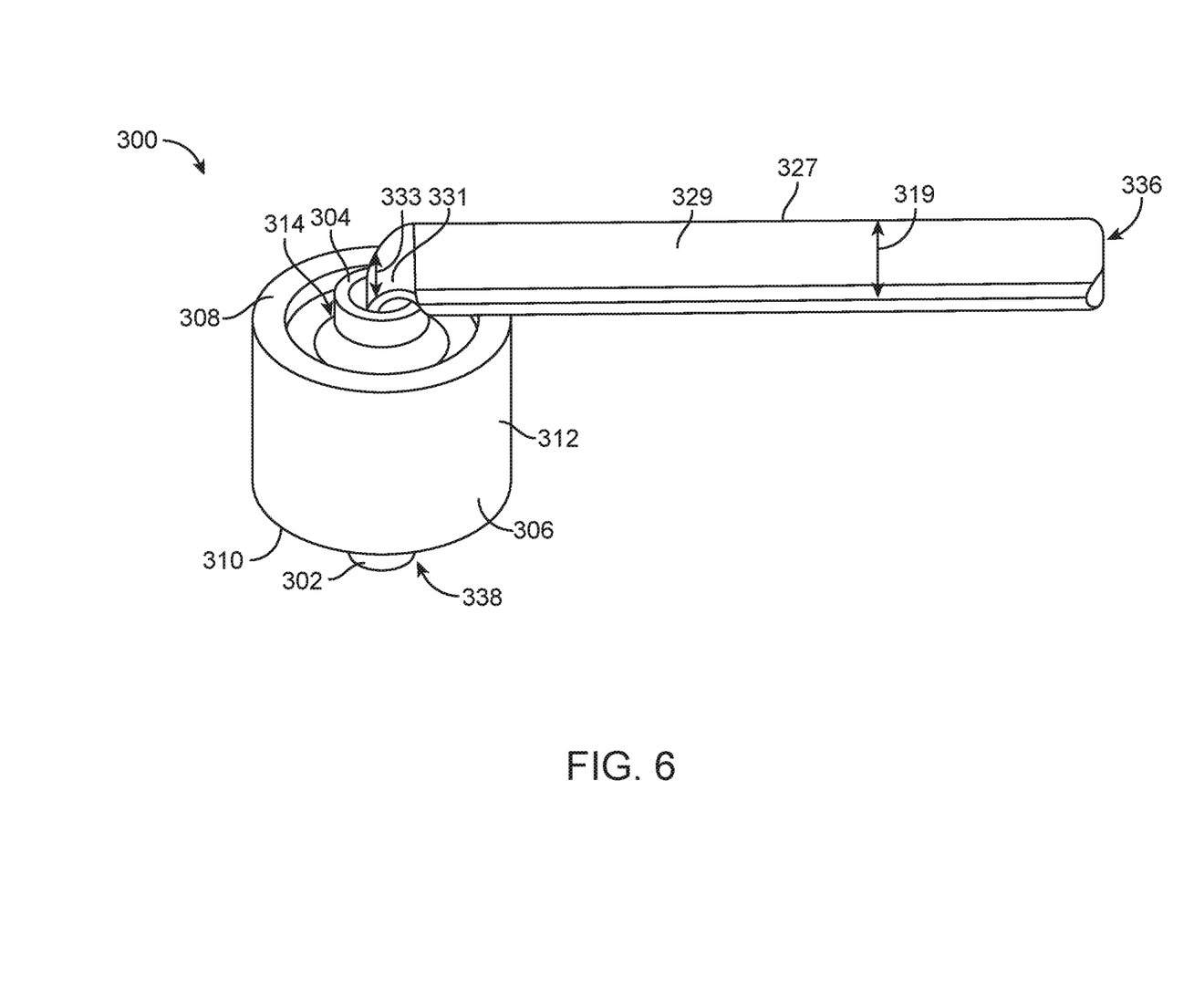
FIG. 6 is a perspective view of one embodiment of a feedthrough device.
Figure 7:
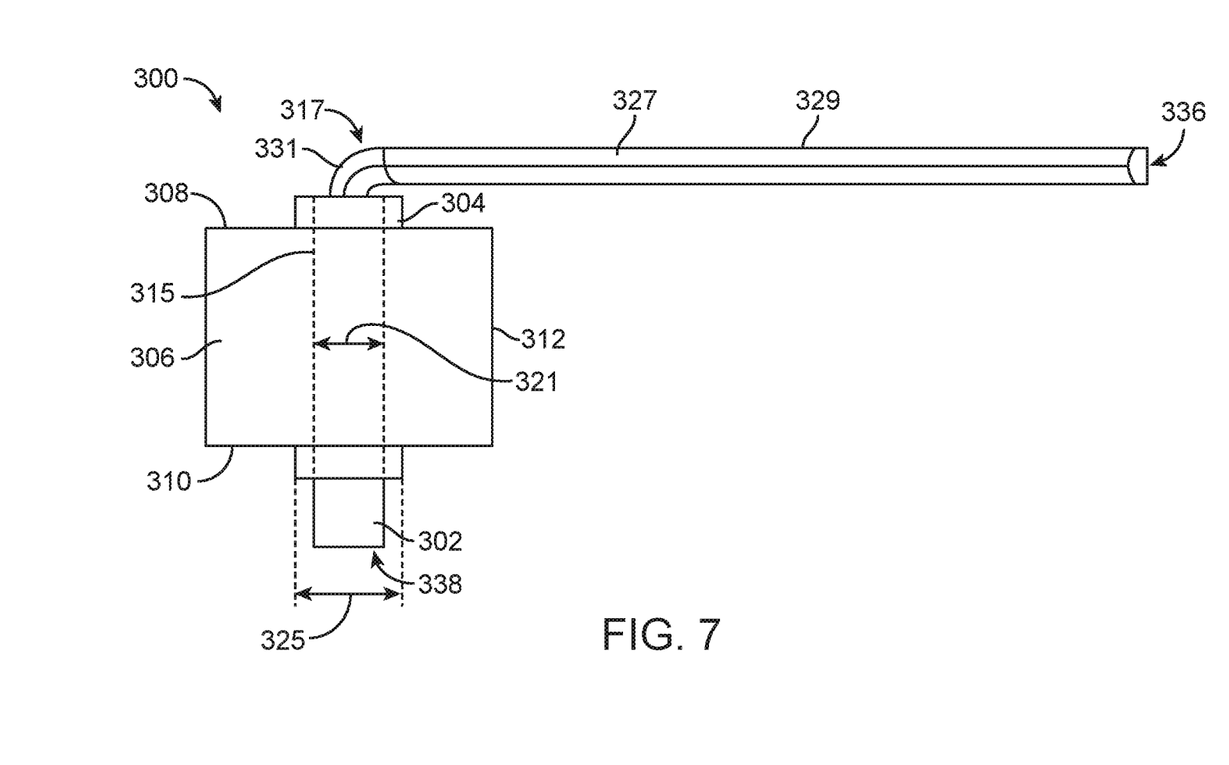
FIG. 7 is a side elevation view of the feedthrough device of FIG. 6.

FIGS. 6-7 illustrate a feedthrough device 300 according to an exemplary embodiment. The feedthrough device 300 is similar in many aspects to the feedthrough devices 200 and 100. The feedthrough device 300 includes a conductor 302, an insulator 304 enclosing at least a portion of the conductor 302, and a body 306 enclosing at least a portion of the insulator 304.

In the illustrated embodiment, the body 306 is all or part of a wall of a sealed housing such as, for example, the end wall of a lithium battery cell housing. The body 306 has longitudinal end faces, referred to herein as a first face 308 (e.g., an exterior face of the battery cell housing), and a second face 310 (e.g., an interior face of the battery housing) longitudinally spaced from the first face 308. A third (e.g., transversely outer) face 312 extends longitudinally between the first face 308 and the second face 310 and broadly defines an outer surface of the body. The body 306 also has a longitudinally extending opening 314 therethrough defining an inner surface of the body as well as a longitudinal axis L of the body.

The conductor 302 has an interior portion 315 surrounded by the insulator 304 and an exterior portion 317 extending beyond the insulator 304 and located outside of the body 306. The exterior portion 317 includes a flattened portion 327 with a diameter (or width) 319 that is greater than the diameter (or width) 321 of the interior portion 315. In some embodiments, the diameter 319 of the flattened portion 327 is substantially the same as the outer diameter (or width) 325 of the insulator 304. In some embodiments, the diameter 319 of the flattened portion 327 is greater than or less than the outer diameter 325 of the insulator 304.

The flattened portion 327 provides a relative large surface area on the exterior portion 317 of the conductor 302. This relatively large surface area is particularly suitable for a welded connection and makes it easier to weld or otherwise attach additional components to the conductor 302 as compared to the feedthrough device 100. Easier welding can reduce assembly time, costs, and complexity.

The exterior portion 317 of the conductor 302 may be bent relative to the interior portion 315 so that the flat surface 329 of the flattened portion 327 is perpendicular to the longitudinal axis of the interior portion 315 of the conductor 302. Such bending may be performed after a crimping or coining operation to secure the conductor 302, the insulator 304, and the body 306 to one another (e.g., the crimping operation described above with reference to the feedthrough device 100). In some embodiments, the flattened portion 327 of the conductor 302 is formed before the conductor 302 is inserted into the body 306 to form a pre-flattened portion. In some embodiments, the flattened portion 327 of the conductor 302 is formed after the conductor 302 is inserted into the body 306. The exterior portion 317 of the conductor 302 includes a neck 331 that connects the interior portion 315 to the flattened portion 327. The diameter (or width) 333 of the neck 331 is less than the diameter 319 of the flattened portion. The smaller diameter 333 of the neck 331 allows the exterior portion 317 to be bent about a relatively small radius, as compared to a conductor in which the flattened portion was the entirety of the exterior portion. The relatively small bend radius helps to keep the flattened portion 327 relatively close to the face 308 of the body 306. This helps to keep the overall size of the feedthrough device 300 small or compact, which can help form devices (e.g., battery packs) in which multiple feedthrough devices are arranged next to one another. In such a device, the individual feedthrough devices could be separately insulated from one another.

Figure 8:
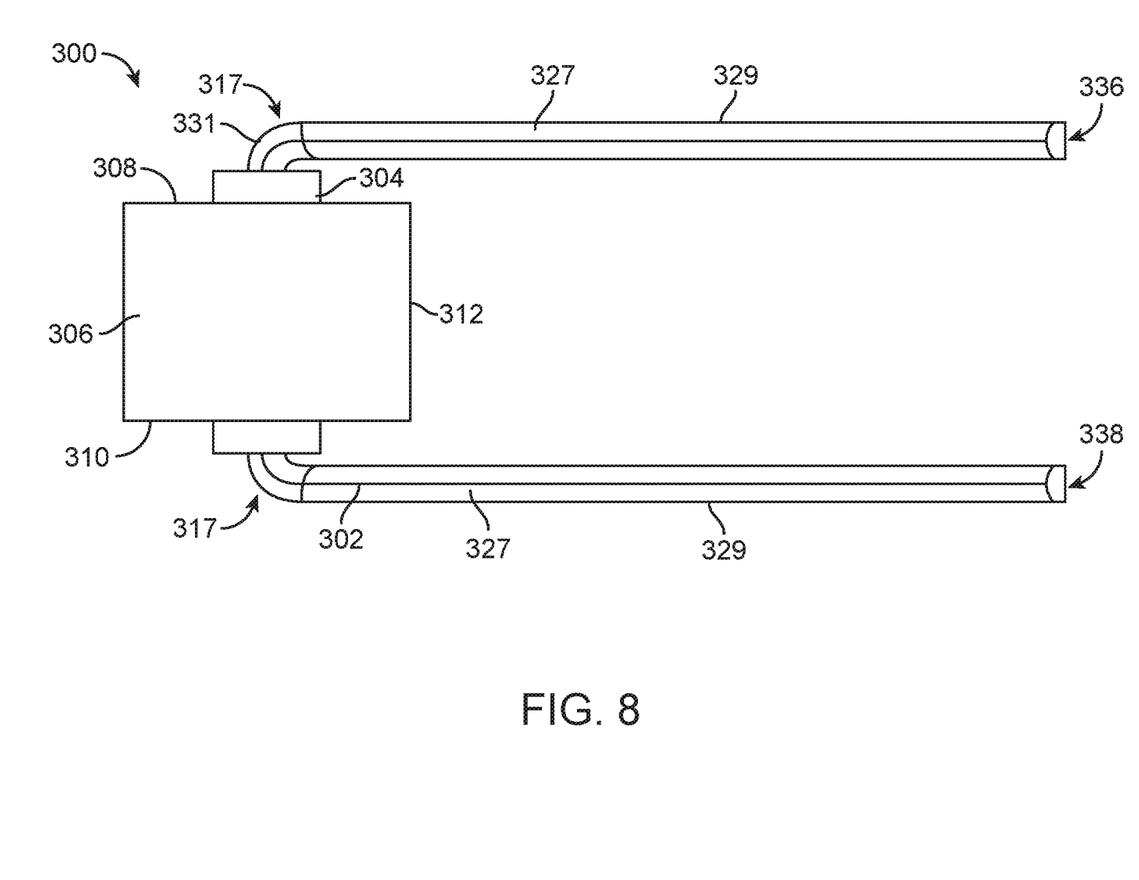
FIG. 8 is a side elevation view of one embodiment of a feedthrough device.

FIG. 8 illustrates an alternative embodiment of the feedthrough device 300 that includes two flattened portions 327, one formed at the first end 336 of the conductor 302 and the other formed at the second end 338 of the conductor 302.

The various embodiments of feedthrough devices discussed herein are similar to one another in many aspects and the specific teachings of one embodiment may be applied to or combined with the teachings of the other embodiments.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense

What is claimed is:

1. A feedthrough device comprising:
   a body having longitudinally spaced first and second end faces and an inner surface defining an opening extending longitudinally through the body;
   a conductor extending within the opening of the body; and
   an insulator extending within the opening of the body transversely intermediate the conductor and the inner surface of the body to insulate the conductor from the body;
   wherein the conductor comprises an interior portion surrounded by the insulator and an exterior portion extending beyond the insulator, the exterior portion having a diameter that is greater than a diameter of the interior portion.

2. The feedthrough device set forth in claim 1, wherein the diameter of the exterior portion is less than an outer diameter of the insulator.

3. The feedthrough device set forth in claim 1, wherein the exterior portion comprises a flattened portion.

4. The feedthrough device set forth in claim 1, wherein the device is for a battery cell having a housing including a wall, the body of the feedthrough device comprising at least part of the wall of the battery cell housing.

5. The feedthrough device set forth in claim 1, wherein the body is fabricated from a first metallic material, the conductor is fabricated from a second metallic material different than the first metallic material, and the insulator is fabricated from a polymeric material.

6. The feedthrough device set forth in claim 1, wherein the insulator at least one of electrically and thermally insulates the body from the conductor.

7. The feedthrough device set forth in claim 1, wherein the exterior portion includes a surface suitable for a welded connection.

8. The feedthrough device set forth in claim 1, wherein the body and the conductor are fabricated from the same metallic material and the insulator is fabricated from a polymeric material.

9. The feedthrough device set forth in claim 1, wherein the conductor comprises an electrical conductor.

10. The feedthrough device set forth in claim 1, wherein the conductor comprises a thermal conductor.

11. A feedthrough device comprising:
   a body having longitudinally spaced first and second end faces and an inner surface defining an opening extending longitudinally through the body;
   a conductor extending within the opening of the body; and
   an insulator extending within the opening of the body transversely intermediate the interior portion of the conductor and the inner surface of the body to insulate the conductor from the body;
   wherein the conductor comprises an interior portion surrounded by the insulator and an exterior portion extending beyond the insulator;
   wherein the exterior portion comprises a flattened portion;
   wherein a diameter of the flattened portion is greater than a diameter of the interior portion; and
   wherein the exterior portion further comprises a neck having a diameter less than the diameter of the flattened portion, the neck connecting the flattened portion to the interior portion.

12. The feedthrough device set forth in claim 11, wherein the flattened portion includes a flat surface that is perpendicular to a longitudinal axis of the interior portion.

13. The feedthrough device set forth in claim 11, wherein the flattened portion includes a flat surface that is angled relative to a longitudinal axis of the interior portion.

14. The feedthrough device set forth in claim 11, wherein the flattened portion is formed in the conductor before the conductor, the insulator, and the body are secured to one another.

15. The feedthrough device set forth in claim 11, wherein the flattened portion is formed in the conductor after the conductor, the insulator, and the body are secured to one another.

16. The feedthrough device set forth in claim 11, wherein the device is for a battery cell having a housing including a wall, the body of the feedthrough device comprising at least part of the wall of the battery cell housing.

17. The feedthrough device set forth in claim 11, wherein the body is fabricated from a first metallic material, the conductor is fabricated from a second metallic material different than the first metallic material, and the insulator is fabricated from a polymeric material.

18. The feedthrough device set forth in claim 11, wherein the insulator at least one of electrically and thermally insulates the body from the conductor.

19. The feedthrough device set forth in claim 11, wherein the conductor further comprises a second exterior portion of the conductor opposite the first exterior portion, the second exterior portion comprising a second flattened portion.

20. The feedthrough device set forth in claim 19, wherein a diameter of the second flattened portion is greater than the diameter of the interior portion.

* * * * *